United States Patent [19]

Pariza et al.

[11] Patent Number: 5,017,614

[45] Date of Patent: May 21, 1991

[54] METHODS OF PREVENTING OXIDATION, QUENCHING SINGLET OXYGEN AND INHIBITING MOLD GROWTH AND NOVEL COMPOSITIONS THEREFOR

[75] Inventors: Michael W. Pariza; Yeong L. Ha, both of Madison, Wis.

[73] Assignee: Wisconsin Alumni Research Foundation, Madison, Wis.

[21] Appl. No.: 313,120

[22] Filed: Feb. 17, 1989

[51] Int. Cl.[5] .................... A61K 31/20; A61K 31/00
[52] U.S. Cl. ...................................... 514/558; 514/2; 426/541
[58] Field of Search .................... 514/549, 558, 2; 426/541, 581, 582, 583, 585, 586, 601, 610, 656; 562/598

[56] References Cited

PUBLICATIONS

Y. L. Ha, N. K. Grimm and M. W. Pariza, in Carcinogensis, vol. 8, No. 12, pp. 1881-1887 (1987).
Y. L. Ha, N. K. Grimm and M. W. Pariza, in J. Agric. Food Chem., vol. 37, No. 1, pp. 75-81 (1987).
Osawa and Namiki (Agric. Biol. Chem. 45: 735,739, 1981).
Pariza, Food Research Institute 1988 Annual Fall Meeting, Oct. 12, 1988.
Science News vol. 135, No. 6, p. 87 (1989).
Hiyoshi, et al., *Chemical Abstracts*, 80, 46644t (1974).
Streitwieser, Jr., et al., *Introduction to Organic Chemistry*, Second Edition, pp. 504-505 (1981).

*Primary Examiner*—John W. Rollins
*Attorney, Agent, or Firm*—Quarles & Brady

[57] ABSTRACT

Methods of preventing oxidation, quenching singlet oxygen and inhibiting mold growth in a product comprises adding to the product a safe and effective amount of an active form of CLA. Active forms of CLA include 9,11-octadecadoenoic acid, 10,12-octadecadienoic acid, active isomers thereof, non-toxic salts thereof; active esters; other active chemical derivatives thereof, and mixtures thereof. Simple methods of making the compositions and novel compositions are also disclosed.

8 Claims, 4 Drawing Sheets

METHODS OF PREVENTING OXIDATION, QUENCHING SINGLET OXYGEN AND INHIBITING MOLD GROWTH AND NOVEL COMPOSITIONS THEREFOR

FIELD OF THE INVENTION

The present invention relates generally to methods and compositions for preventing oxidation, quenching singlet oxygen and inhibiting mold growth, and, more particularly to methods and compositions which can be used in natural food products.

BACKGROUND OF THE INVENTION

Among the antioxidants most widely used in food products are the compounds butylated hydroxyanisole (BHA) and butylated hydroxytoluene (BHT). BHT is also used as an antioxidant in animal feeds, petrol products, synthetic rubbers, plastics, animal and vegetable oils and soaps.

Both BHA and BHT are relatively non-toxic; however, they are not naturally occurring compounds and cannot be used in true "natural" foods.

Among the compounds most widely used to prevent yeast and mold growth are sorbic acid and its potassium salt. These compounds are relatively non-toxic but they too are not naturally occurring and cannot be used in true "natural" foods.

There is a need for safe and effective methods of preventing oxidation in food, as well as, a natural, safe and effective method of preventing mold growth in food. There also is a need for safe and effective compositions for use in such methods.

BRIEF SUMMARY OF THE INVENTION

The primary objects of the present inventions are to disclose natural, safe and effective methods of inhibiting oxidation, quenching singlet oxygen and inhibiting mold growth.

Further objects are to disclose novel compositions for use in those methods and a simple, inexpensive method of preparing such compositions.

The methods of the present invention may take several embodiments. In one embodiment, the antioxidant, singlet oxygen quenching agent, and mold growth inhibitor is added to the product. And, in a second embodiment, the antioxidant, singlet oxygen quenching agent, and mold growth inhibitor is formed in situ in the product.

The antioxidants, singlet oxygen quenching agents, and mold inhibiting compositions of the present invention are those containing the free conjugated linoleic acids (CLA) 9,11-octadecadienoic acid and 10,12-octadecadienoic acid. Active forms of CLA also include compositions containing the active isomers of CLA; non-toxic salts thereof; active esters and other active chemical derivatives thereof; and mixtures thereof. The discovery that these compositions are antioxidants and that they quench singlet oxygen and that they inhibit mold growth was completely unexpected and could not have been predicted from current chemical theory.

The free acid forms of the compositions of the present invention are preferably prepared by reacting linoleic acid with a protein, such as whey protein, which is capable of effecting the transformation of linoleic acid to the desired compositions at temperatures up to about 85° C. The non-toxic salts of the free acids may be made by reacting the free acids with a non-toxic base.

Triglyceride esters may be prepared by reacting a triglyceride containing linoleic acid, such as corn oil, with a protein capable of effecting the transformation of linoleic acid to the active material, such as whey protein. Similar methods can be used to prepare other esters, such as methyl or ethyl esters.

The antioxidant and mold growth inhibiting compounds of the present invention are not all new compounds. The free conjugated linoleic acids (CLA) have been previously isolated from fried meats and described as anticarcinogens by Y. L. Ha, N. K. Grimm and M. W. Pariza, in Carcinogensis Vol. 8, No. 12, pp. 1881-1887 (1987). Since then, they have been found in some processed cheese products. Y. L. Ha, N. K. Grimm and M. W. Pariza, in J. Agric. Food Chem., Vol. 37, No. 1, pp. 75-81 (1987). However, the non-toxic salts of the CLA, such as the sodium and potassium salts, are believed to be novel compounds.

DESCRIPTION OF PREFERRED EMBODIMENT

In the preferred methods of the present invention, a safe and effective amount of one or more of the compositions of the present invention are either added to a product or generated in situ in the product by the reaction of linoleic acid and a protein capable of effecting the transformation of linoleic acid to the active material, such as whey protein.

Figure 1:
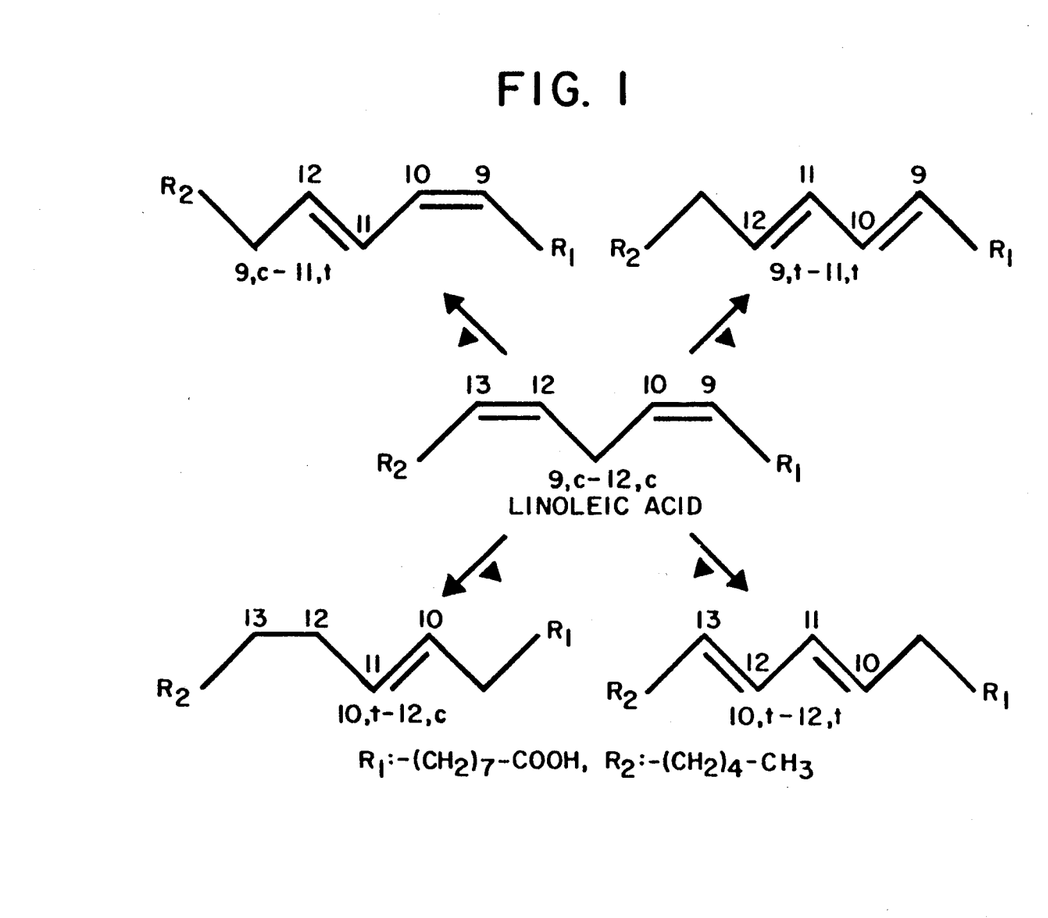
FIG. 1 shows a model for the formation of CLA from linoleic acid.

A form of CLA suitable for use in natural foods is preferably prepared by reacting roughly equivalent amounts of a natural source containing linoleic acid, such as butter fat, with milk whey protein at ambient temperatures. The reaction proceeds quickly even when the ingredients are simply intimately mixed. FIG. 1 shows a model for the formation of CLA from linoleic acid.

The CLA obtained by the practice of the preferred method of preparation contains one or more of the 9,11-octadecadienoic acids and/or 10,12-octadecadienoic acids and active isomers thereof. It may be free or bound chemically through ester linkages. CLA which is heat stable can be used as is, or dried and powdered in salt form. CLA is readily converted into a non-toxic salt, such as the sodium or potassium salt, by reacting chemically equivalent amounts of the free acid with an alkali hydroxide at a pH of about 8 to 9.

CLA and its active non-toxic derivatives, such as the non-toxic salts, can be added to products to inhibit oxidation mediated by free radicals or by singlet oxygen in amounts roughly equivalent to the amounts of BHA or BHT, that are now being used. The exact amount to be added, of course, depends upon the form of CLA employed, the nature of the product, the packaging, and the conditions of storage and use. Generally, the amount employed with CLA and its non-toxic salts will range from about one part per million (ppm) to about 1,000 ppm of product. Like BHA and BHT, the CLA is oil soluble. In contrast to BHA and BHT, CLA is a naturally derived normal constituent of the human diet (including human breast milk).

When used for its mold growth inhibiting properties, CLA or its active derivatives are added to the product to be protected in safe and effective amounts. The exact amount to be added will, of course, depend upon the nature of the product, the packaging and the conditions of storage and use. Generally, the amount employed with CLA and its non-toxic salts will range from about 1,000 ppm to about 10,000 ppm per gram of product. CLA and its non-toxic salts appear to be as effective as sorbic acid or potassium sorbate at similar concentrations.

The exact mechanisms by which the CLA acts as an antioxidant or to quench singlet oxygen are not known. However, it is believed to somehow tie up and defuse free radicals and singlet oxygen. A possible mechanism of action for CLA as an antioxidant is based on the report of Osawa and Namiki (Agric. Biol. Chem. 45: 735-739, 1981). In that report a novel diketone with antioxidant activity was isolated from *Eucalyptus* leaves and was determined chemically to be n-tritriacontan-16, 18-dione. It is proposed that a similar novel diketone with antioxidant activity may form when CLA is exposed to oxygen. The diketone would result from the reaction of molecular oxygen and activated oxygen species with the conjugated double bond system of CLA. The mechanism by which it inhibits mold growth is not known.

While any source of linoleic acid can be used to prepare CLA, the highest yields are obtained when a source rich in linoleic acid, such as corn oil or safflower oil, are used.

The preferred protein which is used to transform linoleic acid to an active form of CLA is whey protein which contains sulfhydryl groups and is, of course, readily available. Other proteins that will transform linoleic acid to CLA can be readily determined without undue experimentation by those skilled in the art. Among such proteins would be those that contain sulfhydryl groups, as well as, nonsulfhydryl containing proteins.

The following examples illustrate the preparation of the CLA by the method of the invention, and the use of CLA to prevent the oxidation of linoleic acid.

EXAMPLE 1

PREPARATION OF CLA

Figure 2:
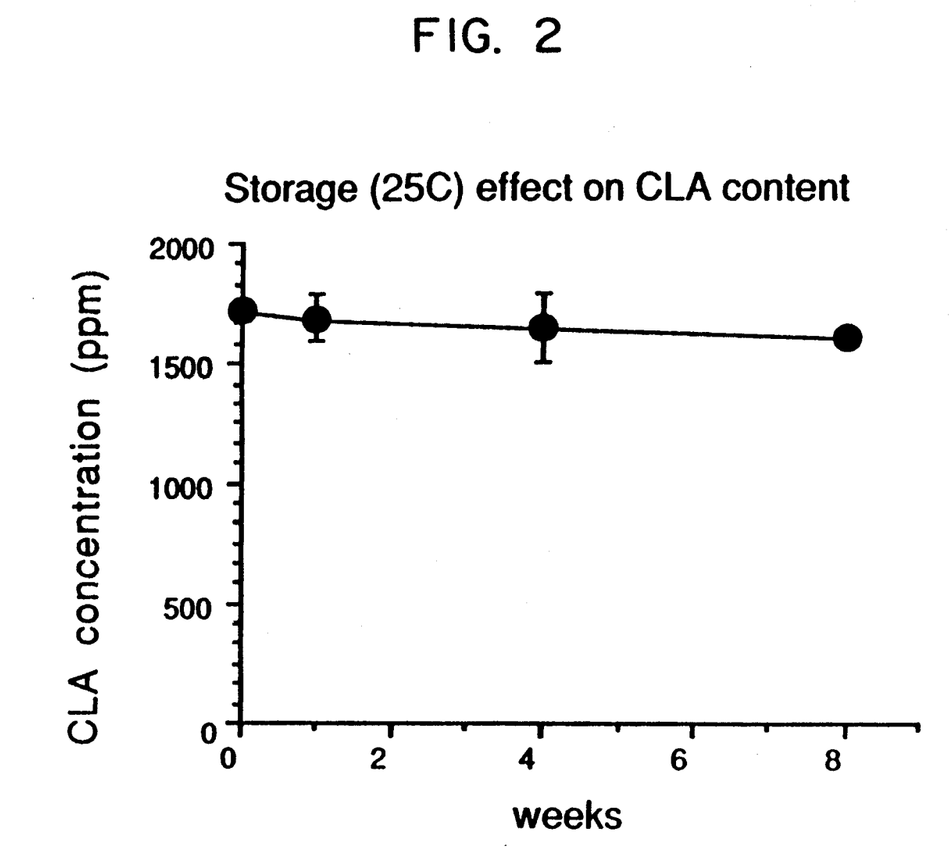
FIG. 2 shows the effect of storage at 25° C. on CLA content produced by combining a linoleic acid source (butter fat) and whey protein.

Forty grams of whey protein and forty five grams of a fat source containing linoleic acid (butter fat) were intimately mixed at ambient temperature and then pasteurized at 85° C. for 5 minutes. After 30 minutes the mixture was assayed for CLA as previously described. The CLA thus formed was stable at 25° C. for up to 8 weeks (See FIG. 2).

EXAMPLE 2

PREPARATION OF POTASSIUM SALT

The potassium salt of CLA was prepared by adding about 50 g. of CLA to 100 ml of water, adjusting to pH 8.5 with 1N KOH, and freeze drying. The resulting product was a white powder.

EXAMPLE 3

PREPARATION OF SODIUM SALT

The sodium salt of CLA was prepared by adding about 50 g. of CLA to 100 ml of water, adjusting to pH 8.5 with 1N NaOH, and freeze drying. The resulting product was a white powder.

EXAMPLE 4

Figure 3:
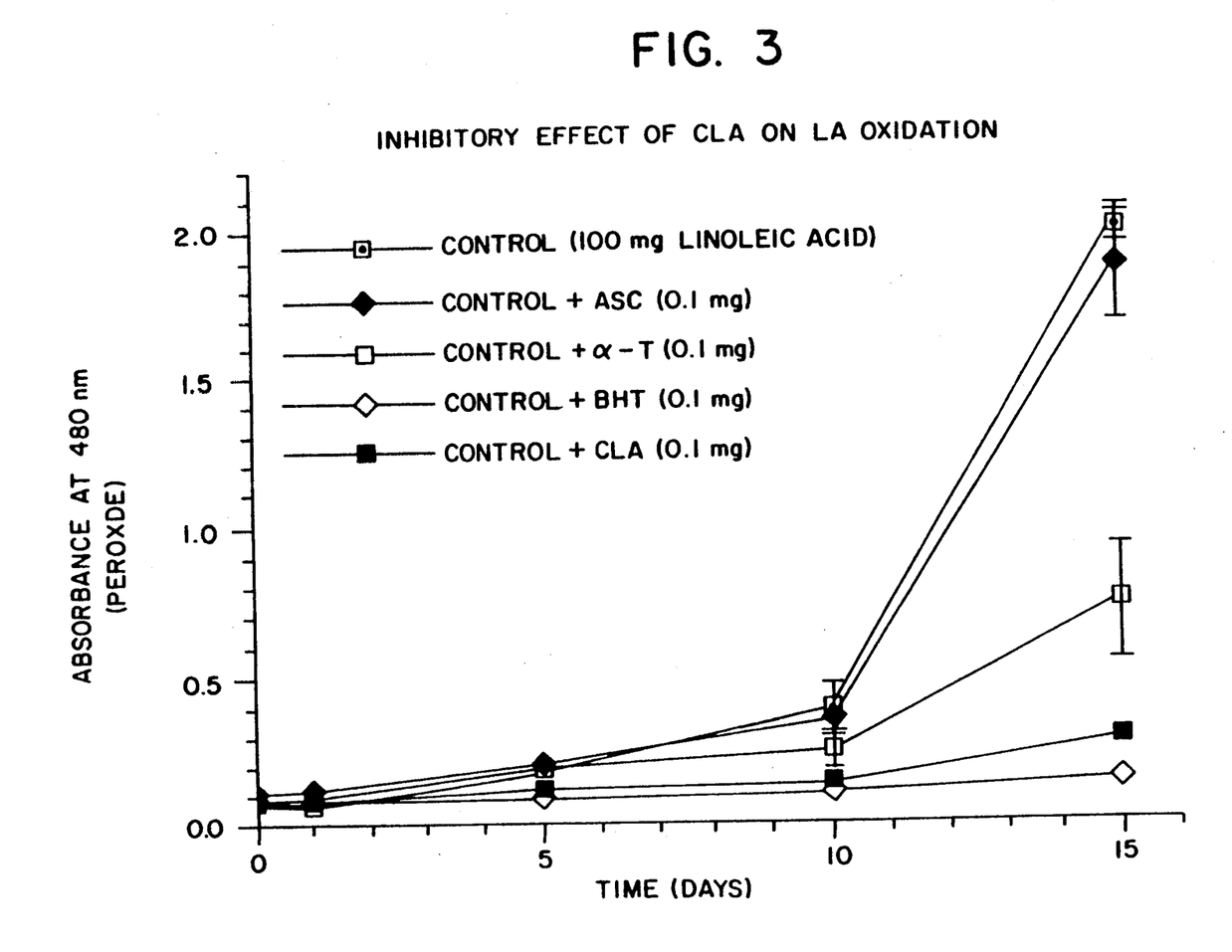
FIG. 3 shows the inhibiting effect of CLA on linoleic acid oxidation as compared to other antioxidants; and, FIG. 4 shows CLA as a singlet oxygen quenching agent.

PREVENTION OF OXIDATION 0.1 mg of CLA prepared by alkali-isomerization of linoleic acid was added to 100 mg of linoleic acid in a reaction medium containing 10 ml of phosphate buffer (pH 8.0, 0.2M); 10.5 ml ethanol and 4.5 ml water. The resulting composition was incubated at 40° C. for up to 15 days. The peroxide produced was measured by the thiocyanate method in which peroxide oxidizes $Fe++$ to $Fe+++$ in the presence of cyanate to give a color exhibiting maximum absorption at 480 nm. The results obtained were equivalent to those obtained with similar amounts of BHA and better than other antioxidants (See FIG. 3).

EXAMPLE 5

INHIBITION OF MOLD GROWTH

The addition of 1% potassium CLA to YM agar medium inhibited mold growth better than 1% potassium sorbate in the same medium under the same conditions.

EXAMPLE 6

SINGLET OXYGEN QUENCHING

Figure 4:
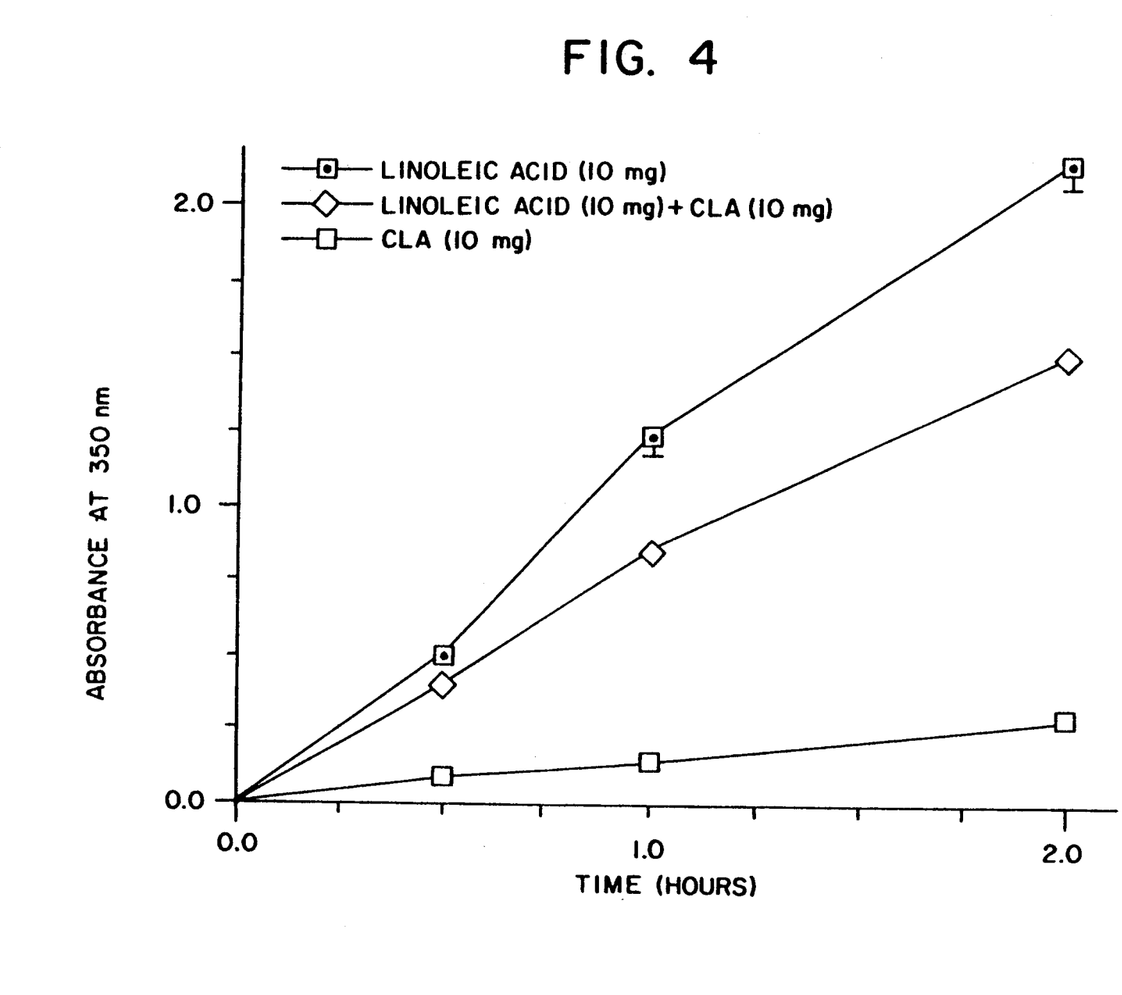

The reaction medium contained (per 5 ml of acetonitrile solvent):
Linoleic Acid (LA): LA (0.007M)+rose bengal ($0.5 \times 10^{-4}$M).
CLA: CLA (0.007M)+rose bengal ($0.5 \times 10^{-4}$M).
LA+CLA: LA (0.007M)+CLA (0.007M)+rose bengal ($0.5 \times 10^{-4}$M).

The sample was illuminated by a tungsten lamp (60 w, 13 cm distance) for various times. The peroxide produced was measured by iodometric method (peroxide oxidize iodine anion ($I^{-1}$) to iodate ($I_2$) to give yellow color exhibiting max absorption at 350 nm. The results are shown in FIG. 4.

Materials and Methods

Materials. Organic solvents (HPLC grade; Burdick and Jackson Chemical Co., Muskegon, MI); 12-hydroxy-c9octadecenoic acid (ricinoleic acid, 99%), 12-hydroxy-t9-octadecenoic acid (ricinelaidic acid, 99%), c9, c12-octadecadienoic acid (linoleic acid, 99%) and other fatty acid standards (Sigma Chemical Company, St. Louis, MO); and trifluoroacetic anhydride, R-(−)-2-phenylbutyric acid (PBA) and 4-phenyl-1,2,4-triazoline-3,5-dione (PTAD) (Aldrich Chemical Co., Milwaukee, Wis.) were used. A 1.0 mg PBA/0.1 ml concentration was prepared with a 2:1 chloroform:methanol (v/v) mixture. Alkali-isomerized linoleic acid was prepared according to the method as previously described (Ha et al., 1987). Cheese and ground beef samples were purchased from the Department of Food Science, University of Wisconsin-Madison (Table I).

Preparation of CLA isomer standards. The methyl ester of t10,c12-octadecadienoate was prepared by crystallization from methyl esters of alkali-isomerized linoleic acid. Methyl t10,t12- and c10,c12-octadecadienoate were prepared from the t10,c12-isomer by iodine and light isomerization. The prepared 10,12-isomers were purified by the normal-phase semi-preparatory HPLC as described below in the HPLC section. A typical semi-preparatory normal-phase HPLC profile of the methyl t10,c12-octadecadienoate prepared exhibited 3 components (peaks 1, 40.1 min; 2, 47.5 min; and 3, 65.1 min), which were present in relative proportions of 89, 2 and 9%, respectively. Subsequent capillary GC analyses, using conditions described in the GC section, of these peaks revealed that peak 1 is a methyl t10,c12-isomer of greater than 95% purity, while peaks 2 and 3 are unknown impurities. The remaining 10,12-geometrical CLA standards were similarly purified by this HPLC procedure.

The 9,11-octadecadienoic acid isomers (c,c; c,t; and t,t) were prepared from ricinoleic acid or ricinelaidic acid, and the individual isomers were separated by the argentation HPLC method.

Preparation of free CLA. This procedure includes extraction and saponification of CLA. Sample material (1 g) containing 1.0 mg PBA (internal standard) was homogenized with 20 ml of 2:1 chloroform:methanol (v/v) for 60 sec in a Polytron homogenizer (Brinkman instruments, Westbury, N.Y.) at medium speed. Another 10 ml of the chloroform:methanol mixture was used to rinse the Polytron probe and combined with the homogenate, followed by addition of 10 ml double distilled water. For milk, 5 g sample, 5.0 mg PBA and 150 ml of chloroform:methanol mixture were used. The homogenate was centrifuged at 2,000 rpm for 30 min (4° C.). The organic layer was separated, dried over $Na_2SO_4$ anhydrous, and roto-evaporated. Total fat content was determined from the residue. Free fatty acids were prepared by heating the fat extracts in 2 ml of 1.0 N-sodium hydroxide in methanol (v/v) in a screw-capped test tube (15×1.5 cm). After being heated in a boiling water bath for 15 min the solution was acidified to pH 1 with 5.5 N-sulfuric acid in water (v/v). The free fatty acids were extracted using 3×10 ml portions of heptane. The organic extract was washed with water, dried over $Na_2SO_4$ anhydrous and the filtered solvent was removed under vacuum with a rotary evaporator.

The effect of this procedure on CLA formation was investigated. When linoleic acid (2.0 mg) was subjected to the procedure, no CLA was detected as determined by UV absorbence at 235 nm using a Beckman DU-50 Spectrophotometer and by the semi-preparatory reversed-phase HPLC as described below. This finding indicates that CLA was not formed as a result of extraction/saponification by our methods.

HPLC separation. Separation and purification of CLA by HPLC were performed at room temperature using a Beckman Model 421A microcontroller system fitted with two solvent delivery modules (Beckman model 110A) and a dual channel UV detector (Micromeritics 788 model; Norcross, GA). Eluent was monitored at 235 or 245 nm. Peak areas were recorded with a Spectra Physics 4270 integrator. CLA in the sample was separated on a semi-preparatory reversed-phase column (Ultrasphere-ODS, 5 μm, 250×10 mm, i.d., Beckman) with a gradient mobile phase (acetonitrile and water) as previously reported (Ha et al., supra). The purification of individual isomers or alkali-isomerized linoleic acid was performed on a normal-phase semi-preparatory column (Ultrasil-$NH_2$, 5 μm, 250 mm×10 mm, i.d., Beckman) using a gradient system. The starting mobile phase (99:1 hexane:ethanol, v/v) and flow rate (1.0 ml/min) were maintained for 20 min and then both hexane proportion and flow rate were linearly increased to 100% and 4.0 ml/min, respectively,, over 20 min. These conditions were held for an additional 40 min and then returned to the starting conditions for 10 min. The system was re-equilibrated at least 10 min prior to the next injection.

Preparation of CLA derivatives. CLA methyl esters were prepared from the free acid form using boron trifluoridemethanol according to the AOCS method Ce2-66 (1973). The PTAD derivative of CLA methyl ester was prepared according to the method of Young, et al., Anal. Chem (1987) 59, 1954–1957 after methylation of CLA.

GC analysis. GC analysis of CLA methyl ester or CLA methyl ester derivatized with PTAD was carried out with a Varian 3700 gas chromatograph fitted with a flame ionization detector (FID) and a Spectra Physics 4270 integrator. The column used was a Supercowax-10 fused silica capillary column (Supelco Inc.): 60 m×0.32 mm, i.d. with a 0.25 μm film thickness. GC conditions consisted of an on-column injection system with helium as the carrier gas at 2 ml/min linear gas flow rate. Temperatures were programmed as follows: oven, 50°–200° C. at 20° C./min and held for 60 min; and injector, 50°–200° C. at 100° C./min after injection. Detector temperature was 250° C. The volume injected ranged from 1.0 to 2.0 μl, containing 0.5 to 5.0 μg CLA/μl.

GC-MS analysis. GC-MS analysis was conducted with a Finnigan 4510 GC-EI/CI automated mass spectrometer system using a splitless injector and a Supercowax-10 capillary column (60 m×0.32 mm, i.d., 2.5 μm film thickness). The column temperature was programmed as specified in the GC analysis section. Electronic impact (EI) ionization and chemical ionization (CI) were carried out at 70 ev and 100° C. as a source temperature. The CI spectrum was obtained using isobutane as a reagent gas. For the analysis of PTAD derivatives of CLA methyl esters, a DB-5 glass capillary column (30 m×0.32 mm, i.d., 1.0 μm film thickness) was used with a temperature program; 60°–250° C. at 10° C./min after one min holding at 60° C. The data were analyzed by a Data General NOVA/4 system equipped with a CDC-CMD disk driver.

GC-FT/IR analysis. GC-FT/IR analysis was performed with a Nicolet model 60S FT/IR using a Supercowax-10 capillary column (60 m×0.32 mm, i.d., 0.25 μm film thickness). GC conditions were the same as those for GC analysis.

CLA quantification. Quantification of individual CLA isomers in a sample was based on the internal standard method. To obtain correction factors (CF) for individual CLA isomers, a reference mixture consisting of known amounts of the isomers plus PBA was subjected to the extraction procedure and reversed-phase HPLC analysis. Pooled CLA and PBA peaks from the HPLC were chromatographed on a capillary GC column (Supercowax-10) after methylation. The CF for the individual isomers was calculated as follows: $CF = (Area_{IS}/Weight_{IS}) \times (Weight_x/Area_x)$, where the subscript IS refers to internal standard and the subscript x refers to a given CLA isomer. Using the $CF_x$, the amount of each CLA isomer in the sample was calculated by the following equation: $ppm_x = [(Area_x/Area_{IS}) \times Weight (mg)_{IS}/sample (gm)] \times CF_x \times 1000$.

RESULTS

GC/HPLC separation. A reversed-phase semipreparative HPLC of the sample effected separation of CLA from the other saturated or unsaturated fatty acids. Subsequent GC analysis of the methylated CLA peak indicated that 7 components (peaks 1 through 7) eluted after linoleic acid; these peaks exhibited identical retention times to those of the methylated alkali-isomerized linoleic acid components. Two approaches were employed to identify the isomers: (1) determination of ECL values of CLA isomers; and (2) spectral analyses of the CLA sample or alkali-isomerized linoleic acid containing unidentified peaks for which standards are not available or are difficult to obtain.

Determination of ECL. A chromatogram showed that the GC profile (Supercowax-10) of the methyl esters of saturated fatty acid standards (C16:0, C17:0, C18:0, C20:0 and C22:0) plus that of a methylated CLA sample. ECL values of CLA methyl ester isomers were determined by plotting carbon numbers vs retention times on semilog paper. The ECL values of CLA methyl esters ranged from 19.49 for peak 1 to 20.01 for peak 7. The ECL values and elution orders have been reported for some of the geometrical/positional isomers of CLA methyl esters separated on a 100-m glass capillary Silar 10C column. The difference in ECL (Delta ECL) remained constant within 0.01–0.03 unit for the isomers tested by both columns. The correlation coefficient (r value) was 0.9995 for the available standards on the two columns. The column (Supercowax-10) that we used is only slightly less polar than a Silar 10C column. Therefore, the ECL data are comparable.

A CLA methyl ester standard was co-chromatographed with a methylated CLA sample containing unidentified peaks. For those peaks that co-chromatographed with a standard CLA methyl ester, identity is set as such. This relationship was then used to determine the identities of the remaining unknown peaks.

According to the ECL relationship and co-chromatographic results, peaks 1, 3, 5, 6 and 7 were identified as methylesters of c9, t11- and/or t9, c11-, t10, c12-, c9, c11-, c10,c12- and t9,t11- and/or t10,t12-octadecadienoates, respectively.

Identification of peaks 2 and 4. The methyl esters of alkali-isomerized linoleic acid or sample CLA were subjected to GC-MS and GC-FT/IR analyses. EI-MS data of peaks 2 and 4 were identical, yielding fragment (M/e) 67 (base peak), 294 (M+), 74, 59 and 262; hence, these isomers could not be distinguished by this method.

Since under normal EI ionization conditions double bonds can migrate prior to fragmentation making it difficult to determine their original positions, others have used CI-MS to identify the double bond position in hydrocarbon chains and fatty acids. CI-MS data of CLA methyl esters of peaks 2 and 4 exhibited a molecular weight of 294 (M+ +1: 295, 100%). Typical M/e for peak 2 were 113 (3%), 213 (5%), 139 (1%) and 239 (12%), and for peak 4 were 99 (5%), 227 (8%), 125 (1%) and 253 (13%). Cleavage between carbons 10 and 11 and 12 and 13 double bond numbered from carboxyl group yielded M/e 113 and 213, respectively. Cleavage between 8–9 and 14–15 single bond carbons produced M/e 139 and 239, respectively. Hence, peak 2 is identified as a 10,12-positional isomer of methyl octadecadienoate. Peak 4 had M/e 99 derived from clevage of the double bond between carbons 11 and 12, M/e 227 from cleavage of the double bond between carbons 13 and 14, M/e 125 derived from single bond cleavage between carbons 9 and 10, and M/e 253 from single bond cleavage between carbons 15 and 16, indicating that this compound is an 11,13-positional isomer.

Additionally, peaks 1 and 5 contained M/e 127, 199, 153 and 225, indicating 9,11-isomers. Similarly, peaks 3 and 6 contained M/e 113, 139, 213 and 239 and were identified as 10, 12-isomers. Peak 7 contained M/e of both 9,11- and 10,12-isomers.

The CLA sample (methyl esters) derivatized with PTAD was chromatographed on a Supercowax-10 column. All peaks of CLA methyl esters disappeared from the GC profile compared with those of underivatized CLA methyl esters. Since PTAD is electrophilic and therefore only reacts with a conjugated double-bond system in hydrocarbon chains or fatty acids via Diels-Alder reaction, peaks 1 through 7 were identified as CLA positional isomers. The PTAD derivatives of CLA methyl esters (molecular weight of 467) that had relatively high polarity were not eluted under these conditions. The Supercowax-10 (polar) column was changed to a DB-5 (nonpolar) column to elute the derivatives. A different elution pattern was obtained from that observed with the former column. This method will not identify positional isomers, but it confirms the presence of the conjugated double-bond in the sample and also indicates the location of CLA methyl esters in the GC chromatogram from the Supercowax-10 column.

The major differences in GC-FT/IR spectra of peaks 2 and 4 were at the 1000–800 $cm^{-1}$ range Sharp absorption at 990 and 945 $cm^{-1}$ (peak 2) and broad absorption at 990 $cm^{-1}$ (peak 4) were observed, indicating that peak 2 is a cis, trans-isomer and peak 4 a cis,cis-isomer.

Based on the results of spectral analyses, co-chromatography and ECL values, peaks 1 through 7 were identified as methyl esters of c9,t11- and/or t9,c11-, c10,t12-, t10,c12-, c11,c13-, c9,c11-, c10,c12- and t9,t11- and/or t10,t12octadecadienoates, respectively.

Application. The newly developed GC/HPLC method to analyze individual CLA isomers was applied to the dairy products and beef. A CLA sample containing PBA was purified on the semipreparatory reversed-phase column. PBA was eluted at 6.2 min and CLA at 40 min. The two pooled peaks were dried over $Na_2SO_4$ anhydrous and the organic solvent was evaporated under nitrogen. After methylation of the residue, it was analyzed by GC. PBA was co-eluted with some impurities on the HPLC column, but these impurities did not interfere with CLA isomer resolutions on the GC column.

Quantification of peaks 2 (c10,t12-isomer) and 4 (c11,c13-isomer) was based on an assumption that CF values of these isomers are equal to the average CF values of the remaining five CLA isomers: 0.17, c9,t11-isomer (peak 1); 0.16, t10,c12-isomer (peak 3); 0.17, c9,c11-isomer (peak 5); 0.16, c10,c12-isomer (peak 6); and 0.17, t9,t11- or t10,t12-isomer (peak 7). Total CLA content among cheeses ranged from 169.3 ppm (Blue cheese) to 1815 ppm (CHEESE WHIZ ®). Of the aged natural cheeses, Parmesan cheese aged more than 10 months contained the highest (622.3 ppm) and Blue cheese aged over 100 days contained the lowest amounts of CLA (169.3 ppm), suggesting a positive relationship between the aging period and CLA content. In general, processed cheese contained more CLA than natural cheese. It is interesting to note that raw and pasteurized whole milk both contained similar amounts of CLA. Grilled ground beef contained 994 ppm of total CLA, while uncooked ground beef contained 561.7 ppm. Fat content ranged from 4.0% (pasteurized whole milk) to 35.5% (cream cheese). Based on total fat, the CLA content ranged from 549.8 ppm (Blue cheese) to 9289.7 ppm (grilled ground beef).

Of the individual isomers, t9,t11-/t10,t12-, c9, t11/t9, c11- and t10,c12-octadecadienoic acids accounted for more than 89% of the total CLA in all measured samples. The t,t-isomers ranged from 49.8% (uncooked ground beef) to 78.1% (cream cheese); however, in milk samples approximately 15% of the CLA was present as t,t-isomers. The remaining CLA isomers (c9,c11-, c10,c12-, c10,t12-, c11,c13) contributed less than 11% of the total CLA in the samples.

Origin of CLA. The origin of CLA in cheese and ground beef is not known. CLA formation may be attributed to (1) free-radical type oxidation of linoleic acid effected by aging, heat treatment and protein quality; and (2) isomerization of linoleic and linoleic acids in the rumen.

Aging processes modify the physio-chemical properties of cheese or beef to give typical characteristics. Examples include the oxidation of fats. Under anaerobic conditions this may occur during heating, where oxidation of linoleic acid in glycerides or phospholipids may be initiated to form an allyl radical. The radical would be stabilized through the formation of its resonance forms which require hydrogens to form a conjugated double-bond system. The hydrogens are attributed to proteins which, in turn, form protein radicals. These radicals may be neutralized by alpha-tocopherol in the lipophilic regions. It is known that when linoleic acid was oxidized by UV irradiation in the presence of albumin, 9, 11-conjugated linoleic acid is formed rather than oxidation products, suggesting the importance of protein as a hydrogen source. The importance of protein in CLA formation is also supported by our finding that lactalbuminand lactoglobulin-enriched cheese contained significantly higher amounts of CLA than other cheeses that were not enriched. CHEESE WHIZ ®, which is enriched with whey concentrate (Table I), contained twice as much CLA as the other processed cheeses. Whey protein contains relatively high levels of lactalbumin and lactoglobulin that could provide a hydrogen source.

CLA isomers that were isomerized from linoleic and linolenic acids in the rumen may contribute directly to the CLA content in cheese or meat. A significant amount of CLA was present in raw whole milk and pasteurized whole milk. A positive correlation has been observed between conjugated dienoic C18 fatty acids of milk with trans isomers and linoleic acid in the diet. These conjugated dienoic fatty acids are also present in butter (1–4.5%) and are directly related to the linolenic acid content in the diet of cows. During biohydrogenation of linoleic or linolenic acid by microorganisms in the rumen, cis-double bonds undergo an extensive isomerization. This may involve a shift in position along with the carbon chain (positional isomerization) or a change of geometrical configuration or both. Isomerization would be the rate controlling step and would determine the final concentration of CLA. In milk or ruminant animal tissues, the isomer ratio is effected by the microbial population in the rumen which, in turn, is influenced by the amount of linolenic acid and/or linolenic acid fed.

Formation of positional/geometrical isomers. The t9,t11- and t10,t12-isomers, and the c9,t11- and t9,c11- isomers could not be separately quantified in this study. However, if we assume that each of the t,t-isomers contributes equally to the total amount of peak 7, and that the total concentration of the t9,c11-isomer co-eluted with c9,t11-isomer in peak 1 is equal to the concentration of the c10,t12-isomer of peak 2, then the following conclusion may be drawn: (1), the molar concentration of the 9,11-positional isomer is identical to the molar concentration of the 10,12-positional isomer; (2), the concentrations of c9,t11- and t11,c12-isomers are equal; (3), there are four major isomers (t9,t11-, c9,t11-, t10,t12- and t10,c12-) and five minor isomers (c9,c11- t9,c11-, c10,c12-, c10,t12- and c11,c13-); and 4), there is a relatively higher concentration (61–78.1% of total CLA in cheese) of t,t-isomers. These conclusions might be explained by the isomerization of linoleic acid and/or linoleic acid geometrical isomers (c9,t12-, t9,t12- and t9,c12-isomers).

Linoleic acid radical containing an unpaired electron on the methylene interrupted carbon (carbon number 11) would stabilize to form resonances via a proton shift. The shift occurs in either the carboxyl group or hydrocarbon terminal direction to make a conjugated double-bond. The probability of the formation of 9,11- or 10,12-isomer is equal due to the distance of the carboxyl group from the double-bond system and/or to the esterfied carboxyl group in the glycerides or phospholipids.

Theoretically, 8 possible geometric isomers of 9,11- and 10,12-octadecadienoic acid (c9,c11; c9,t11; t9,c11; t9,t11; c10,c12; c10,t12; t10,c12 and t10,t12) would form from the isomerization of c9,c12-octadecadienoic acid. As a result of the isomerization, only four isomers (c9,c11; c9,t11; t10,c12; and c10,c12) would be expected. However, of the four isomers, c9,t11- and t10,c12- isomers are predominantly produced during the autoxidation or alkali-isomerization of c9,c12-linoleic acid due to the co-planar characteristics of 5 carbon atoms around a conjugated double-bond and spatial conflict of the resonance radical. The remaining two c,c-isomers are minor contributors.

The relatively higher distribution of the t,t-isomers of 9,11- or 10,12-octadecadienoic acid in the sample apparently resulted from the further stabilization of c9,t11- or t10,c12-geometric isomers, which is thermodynamically preferred, during an extended processing time or long aging period. Additionally the t,t-isomer of 9,11- or 10,12-octadecadienoic acid that was predominantly formed during the isomerization of linoleic acid geometrical isomers (t9,t12-, c9,t12- and t9,c12-octadecadienoic acid) may influence the final ratio of the isomers or the final CLA content in the samples. These linoleic acid geometrical isomers accounted for up to 11% of the milk fat and for 13.6% of the linoleic acid content in beef. In the case of milk, we observed only 15% of the total CLA content was the t,t-isomers far lower than for the other samples. The reason for this may be that rumen microorganisms preferentially isomerized c9,c12-octadecadienoic acid to c9,t11-octadecadienoic acid. Subsequent pasteurization of the milk was not sufficient to effect the stabilization of c,t-isomers to the t,t-isomeric forms.

Linoleic acid geometrical isomers also influence the distribution of minor contributors (c,c-isomers of 9,11- and 10,12-, t9,c11- and c11,t12-octadecadienoic acids). The 11,13-isomer might be produced as a minor product from c9,c12-octadecadienoic acid or from its isomeric forms during processing.

The methods combining reverse-phase HPLC with GC may be used to determine CLA and its isomeric forms in food products. Such information should be of interest given the anticarcinogenic properties of CLA under certain conditions in animal experiments, the fact that CLA has been isolated from human milk, serum, bile and duodenal juice and our discovery that it is an effective antioxidant and mold growth inhibitor.

TABLE I

Products studied

| Sample | Descriptive Characteristics |
| --- | --- |
| 1. Parmesan cheese (Grated) | Part-skim milk, cheese culture, enzymes, aged over 10 months |
| 2. Cheddar cheese (American) | Whole milk, cheese culture, enzymes, aged over 6 months |
| 3. Romano cheese (Grated) | Part-skim cow milk, cheese culture, enzymes, aged over 5 months |
| 4. Blue cheese | Whole milk, cheese culture, enzymes, aged over 100 days |
| 5. Past. proc. cheese (American) | American cheese, milkfat |
| 6. Cream cheese | Pasteurized milk, cream cheese culture |
| 7. Cheese spread (Roka blue) | Pasteurized milk, milkfat, cream cheese |
| 8. Cheese Whiz ® (Kraft) | Cheddar cheese, low moisture part-skim Mozzarella cheese, whey concentrate |
| 9. Milk | |
| Pasteurized whole | Cow's milk |
| Non-pasteurized whole | Cow's milk |
| 10. Ground beef | uncooked or grilled |

CLA is naturally present in cheese but is esterified in triglycerides. To be effective in inhibiting mold growth, we believe that the free acid or salt form of CLA must be present.

It will be readily apparent to those skilled in the art that a number of modifications or changes may be made without departing from the spirit and scope of the present invention. Therefore, the invention is only to be limited by the claims.

We claim:

1. A method of preventing oxidation, quenching singlet oxygen and inhibiting mold growth in a fatty acid containing product which comprises adding to said product a safe and effective amount of CLA.

2. A method of claim 1 in which the CLA is added by forming it in situ by adding sufficient linoleic acid and a protein containing sulfhydryl groups to the product to form the CLA.

3. A method of preventing oxidation, quenching singlet oxygen, and inhibiting mold growth in a food product which comprises adding to said food product a safe and effective amount of CLA.

4. A method of preventing oxidation, quenching singlet oxygen and inhibiting mold growth in a food product which comprises adding to said food product sufficient linoleic acid and a protein containing sulfhydryl groups to form in situ an effective amount of CLA.

5. A method of claim 4 in which the protein is whey protein.

6. A method of preparing CLA, which is an antioxidant, a singlet oxygen quenching agent and a mold growth inhibitor, which method comprises reacting roughly equivalent amounts of linoleic acid and a protein containing sulfhydryl groups at ambient temperatures to form the CLA.

7. A method of claim 6 in which the protein is whey protein.

8. A method of inhibiting mold growth in a food product which comprises adding to said food product a safe and effective amount of CLA to inhibit mold growth.

* * * * *